United States Patent
Toniolo

(10) Patent No.: US 11,261,468 B2
(45) Date of Patent: Mar. 1, 2022

(54) MICROBIOLOGICAL PROCESS FOR THE PREPARATION OF AMIDES

(71) Applicant: COLUMBIA SRL, Monticello Conte Otto (IT)

(72) Inventor: Stefano Toniolo, Monticello Conte Otto (IT)

(73) Assignee: COLUMBIA SRL, Monticello Conte Otto (IT)

( * ) Notice: Subject to any disclaimer, the term of this patent is extended or adjusted under 35 U.S.C. 154(b) by 54 days.

(21) Appl. No.: 16/758,481

(22) PCT Filed: Nov. 9, 2018

(86) PCT No.: PCT/EP2018/080711
§ 371 (c)(1),
(2) Date: Apr. 23, 2020

(87) PCT Pub. No.: WO2019/096677
PCT Pub. Date: May 23, 2019

(65) Prior Publication Data
US 2020/0248216 A1 Aug. 6, 2020

(30) Foreign Application Priority Data

Nov. 14, 2017 (IT) .................. 102017000129625

(51) Int. Cl.
*C12P 13/02* (2006.01)
*C12N 1/20* (2006.01)
*C12R 1/01* (2006.01)

(52) U.S. Cl.
CPC .............. *C12P 13/02* (2013.01); *C12N 1/205* (2021.05); *C12R 2001/01* (2021.05)

(58) Field of Classification Search
CPC ........... C12P 13/02; C12N 1/205; C12N 9/88; C12R 2001/01; C12Y 402/01084
See application file for complete search history.

(56) References Cited

FOREIGN PATENT DOCUMENTS

| WO | 02055670 | A1 | 7/2002 |
|---|---|---|---|
| WO | 02070717 | A2 | 9/2002 |
| WO | 03066800 | A2 | 8/2003 |
| WO | 2006062189 | | 6/2006 |
| WO | 2017199200 | | 11/2017 |

OTHER PUBLICATIONS

Kubac et al., "Biotransformation of nitriles to amides using soluble and immobilized nitrile hydratase from Rhodococcus erythropolis A4", Journal of Molecular Catalysis B: Enzymatic, 2007, vol. 50, No. 2-4. pp. 107-113.

Prasad et al., "Nitrile hydratases (NHases): At the interface of academia and industry", Biotechnology Advances, 2010, vol. 28, No. 6, pp. 725-741.

Su et al., "*Rhodococcus biphenylivorans* sp. nov., a polychlorinated biphenyl-degrading bacterium", Antonie Van Leeuwenhoek, 2014, vol. 107, No. 1, pp. 55-63.

Su et al., "Identification, characterization and molecular analysis of the viable but nonculturable Rhodococcus biphenylivorans", Scientific Reports, 2015, vol. 5, pp. 1-11.

International Search Report and Written Opinion for Corresponding International Application No. PCT/EP2018/080711 (13 Pages) (dated Dec. 6, 2018).

*Primary Examiner* — Delia M Ramirez
(74) *Attorney, Agent, or Firm* — Lucas & Mercanti, LLP

(57) ABSTRACT

A microbiological process for the preparation of amides from the corresponding nitriles by enzymatic hydrolysis with nitrile hydratase enzyme from a bacterial strain of *Rhodococcus biphenylivorans* species is described.

12 Claims, No Drawings

MICROBIOLOGICAL PROCESS FOR THE PREPARATION OF AMIDES

This application is a 371 of PCT/EP2018/080711, filed Nov. 9, 2018, which claims the benefit of Italian Patent Application No. 102017000129625, filed Nov. 14, 2017.

DESCRIPTION

Field of the Invention

The present invention relates to a process for the preparation of amides and, more particularly, to a process for the preparation of amides from the corresponding nitriles by enzymatic hydrolysis with nitrile hydratase enzyme from a bacterial strain of *Rhodococcus* biphenylivorans species.

Background of the Invention

Nitriles are important precursors for the synthesis of amides and carboxylic acids, widely used as pharmaceutical active ingredients or as advanced intermediates for their synthesis.

The chemical hydrolysis of nitriles from carboxylic acids, which proceeds through the intermediate amide, requires drastic conditions such as strong bases or acids at high temperatures (100° C.) and long reaction times. At the beginning the amide is formed but, as also the amides are hydrolyzed by acid or basic treatment, the carboxylic acid forms quickly. In view of the conditions to be used, the chemical hydrolysis is not often suitable for the preparation of pharmaceutical active ingredients or advanced intermediates thereof because these compounds often have one or more asymmetric centers and/or other functional groups.

The chemical hydrolysis can be also not suitable for obtaining amides because the hydrolysis procedure must be stopped to prevent the conversion to acid.

As an alternative to chemical hydrolysis, enzymatic hydrolysis may be used.

Several enzymatic processes for the conversion of nitriles to amides by using bacterial strains which produce nitrile hydratase enzyme (also referred to as NHase) are known in the literature.

However, these processes generally apply to specific classes of nitriles only and do not allow their application on substrates having chemical characteristics which may be also very different each other.

Therefore, there is still the need of an enzymatic method for the conversion of nitriles to amides which is applicable to a wide variety of nitriles with good yields.

We have now found that the nitrile hydratase enzyme produced by the strain of *Rhodococcus biphenylivorans* named "Palladio 22" and deposited on Dec. 4, 2016 in the Collection of Microorganisms BCCM (Belgian Coordinated Collections of Microorganisms)-LMG with deposit number LMG P-29520 in compliance with the requirements of the Budapest Treaty is capable to convert a wide variety of nitriles to the corresponding amides with good chemoselectivity, regioselectivity and stereoselectivity.

The strain of *Rhodococcus* biphenylivorans named "Palladio 22" has been already described to be useful in the production of acrylamide in the International patent application WO2017199200 filed by the present Applicant and published on Nov. 23, 2017.

SUMMARY OF THE INVENTION

Therefore, object of the present invention is a microbiological process for the preparation of amides of formula

comprising the reaction of a nitrile of formula

with the nitrile hydratase enzyme produced by the bacterial strain Rhodococcus biphenylivorans named "Palladio 22" deposited in the Collection of Microorganisms BCCM-LMG with deposit number LMG P-29520, wherein at least one among R, R' and R" is different from hydrogen;

R, R' and R", the same or different each other, are independently selected among hydrogen, $C_1$-$C_6$ alkyl, $C_1$-$C_6$ alkoxy, $C_1$-$C_6$ alkoxycarbonyl, $C_2$-$C_6$ alkenyl, $C_3$-$C_6$ cycloalkyl optionally containing a =O group, R'"CO—, heterocycle with 3 to 6 atoms of which at least one is N or O, arylsulfonyl, $C_1$-$C_6$ alkylsulfonyl, aryl, arylaminocarbonyl and $C_1$-$C_6$ alkylaminocarbonyl group;

R'" is $C_1$-$C_6$ alkyl, aryl, amino, hydrazino;

each R, R', R" and R'", when different from hydrogen, being optionally substituted by one or more substituents selected among halogen, nitrile, amino, $C_1$-$C_6$ alkylamino, hydroxy, $C_1$-$C_6$ alkoxy, aryl groups; provided that the compound of formula I is not acrylamide.

DETAILED DESCRIPTION OF THE INVENTION

In the present context, the conversion reaction of the nitrile to amide will be indicated with the term "hydrolysis" more commonly used in the art even if it would be more correct to refer to such a conversion reaction as to a "hydration". The two terms will be used herein interchangeably by giving them the same meaning.

The term "$C_1$-$C_6$ alkyl" is used as commonly understood by a skilled in the art and refers to a chemical entity having a carbon skeleton or a main carbon chain comprising a number from 1 to 6 (including all the single integers within the range as well as the integers 1 and 6) of carbon atoms. Each $C_1$-$C_6$ alkyl can be linear or branched.

The term "branched" is used as commonly understood by a skilled in the art and refers to a chemical entity having a skeleton or a main chain which splits into more than one contiguous chain. The portions of the skeleton or of the main chain which split into more than one direction can be linear, cyclic or any combinations thereof. Non limiting examples of a branched alkyl are tert-butyl, isobutyl and isopropyl.

The term "linear" is used as commonly understood by a skilled in the art and refers to a chemical entity having a skeleton or a main chain which does not split into more than one contiguous chain. Non limiting examples of linear alkyls are methyl, ethyl, n-propyl and n-butyl.

The term "$C_3$-$C_6$ cycloalkyl" is used as commonly understood by a skilled in the art and refers to a compound or to a chemical entity in which at least a portion of the carbon skeleton or main chain of the chemical entity is bound to form a ring of atoms which are linked together. The atoms do not need to be all directly linked each other, but rather they need to be directly linked to at least other two atoms. Non limiting examples of $C_3$-$C_6$ cycloalkyl include cyclopropane, cyclobutane, cyclopentane and cyclohexane.

Analogously, the term "$C_3$-$C_6$ heteroalkyl" is to be understood to refer then to a compound or to a chemical entity in which at least a portion of the skeleton or of the main atom chain of the chemical entity, which includes at least a heteroatom, is bound to form a ring of atoms which are linked together. The atoms do not need to be all directly linked each other, but rather they need to be directly linked to at least other two atoms.

The terms "aryl" and "heteroaryl" are used as commonly understood by a skilled in the art and refer to a compound or to a chemical entity in which at least a portion of the skeleton or of the main atom chain of the chemical entity is bound to form an aromatic ring.

As used herein, $C_1$-$C_6$ alkyl includes, for example and without limitations, methyl, ethyl, n-propyl, i-propyl, sec-propyl, n-butyl, i-butyl, sec-butyl, t-butyl, n-pentyl, i-pentyl, sec-pentyl, t-pentyl, n-hexyl, i-hexyl, 1,2-dimethylpropyl, 2-ethylpropyl, 1-methyl-2-ethylpropyl, 1-ethyl-2-methylpropyl, 1,1,2-trimethylpropyl, 1,1,2-triethylpropyl, 1,1-dimethylbutyl, 2,2-dimethylbutyl, 2-ethylbutyl, 1,3-dimethylbutyl, 2-methylpentyl, 3-methylpentyl, sec-hexyl, t-hexyl.

Non limiting examples of $C_2$-$C_6$ alkenyl include vinyl, allyl, isopropenyl, 1-propen-2-yl, 1-buten-1-yl, 1-buten-2-yl, 1-buten-3-yl, 2-buten-1-yl, 2-buten-2-yl.

Non limiting examples of $C_3$-$C_6$ cycloalkyl include cyclopropyl, cyclobutyl, cyclopentyl, cyclohexyl.

Non limiting examples of aryl include phenyl (Ph) and naphthyl.

As used herein, non limiting examples of heterocycle groups include pyrrolidinyl, pyrrolinyl, piperidinyl, piperazinyl, imidazolinyl, pyrazolidinyl, imidazolidinyl, morpholinyl, tetrahydropyranyl, azetidinyl, oxetanyl, phthalimide and succinimide. Non limiting examples of heteroaryl groups include pyrrolyl, pyridinyl, pyridazinyl, pyrimidinyl, pyrazinyl, imidazolyl, oxazolyl.

In a preferred embodiment, the process object of the present invention applies to the preparation of amides of formula I wherein at least one among R, R', R" and R'" is or contains a functional group sensitive to hydrolysis or solvolysis under acid, basic or neutral catalysis and environment selected among an additional nitrile group, an ester group, an amido group, a haloalkyl group, an ammonium salt.

The high selectivity of the process object of the present invention advantageously allows to carry out the conversion of the nitrile group only, without altering other functional groups present in the starting compound of formula II.

In particular, no modifications occur to functional groups which are practically impossible to preserve totally or without producing by-products and/or impurities if they undergone chemical hydrolysis catalyzed by acids or bases.

This feature is peculiar to the process object of the present invention and it represents its more advantageous and innovative characteristic.

In the following table some specific examples of nitriles which can be used in the microbiological process object of the present invention are provided, without any limitative purpose. All the nitriles in the table are known compounds and most of them are used as intermediates in processes for the preparation of pharmaceutical active ingredients (API).

TABLE

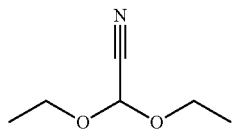

6136-93-2

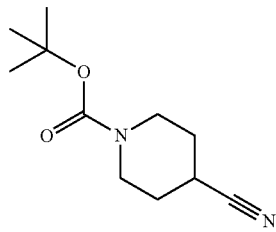

91419-52-2

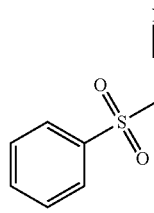

7605-28-9

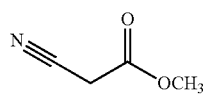

105-34-0

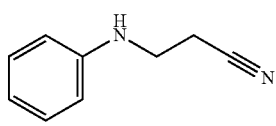 [SMILES: N#CCCNc1ccccc1]

1075-76-9

TABLE-continued

| Structure | CAS |
|---|---|
| 1-benzyl-4-(methylamino)piperidine-4-carbonitrile | 1075-76-9 |
| 4,4-dimethoxybutanenitrile (3,3-dimethoxypropanenitrile) | 57597-62-3 |
| 2-aminobenzyl cyanide | 2973-50-4 |
| cyanoacetohydrazide | 140-87-4 |
| 2-(cyanomethyl)benzonitrile | 3759-28-2 |
| (isopropylsulfonyl)acetonitrile | 120069-21-8 |
| ethyl (S)-5-cyano-3-hydroxypentanoate | 141942-85-0 |
| 5-oxohexanenitrile | 10412-98-3 |
| 2-cyano-N-phenylacetamide | 621-03-4 |
| 1-phenyl-4-oxocyclohexane-1-carbonitrile | 25115-74-6 |
| methyl 1-cyanocyclopentane-1-carboxylate | 40862-12-2 |

TABLE-continued
| | |
|---|---|
| 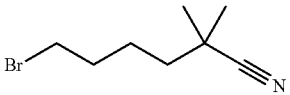 | 53545-96-3 |
| 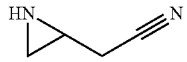 | 109-82-0 |
| 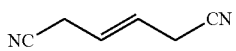 | 1119-85-3 |
| 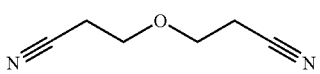 | 1656-48-0 |
| 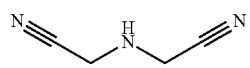 | 628-87-5 |
| 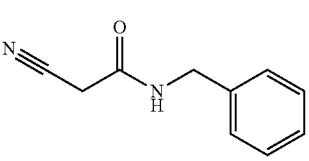 [SMILES: N#CCC(=O)NCc1ccccc1] | 10412-93-8 |
| 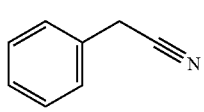 | 140-29-4 |
| 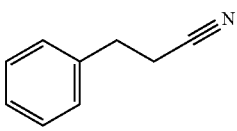 | 645-59-0 |
| 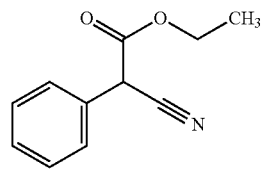 | 4553-07-5 |
| 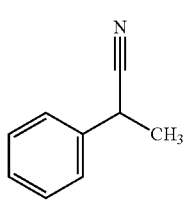 | 1823-91-2 |
| 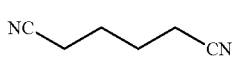 | 111-69-3 |
| 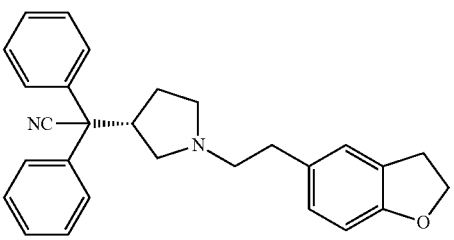 [SMILES: N#CC(c1ccccc1)(c1ccccc1)[C@@H]1CCN(CCc2ccc3c(c2)CCO3)C1] | 252317-48-9 |

TABLE-continued

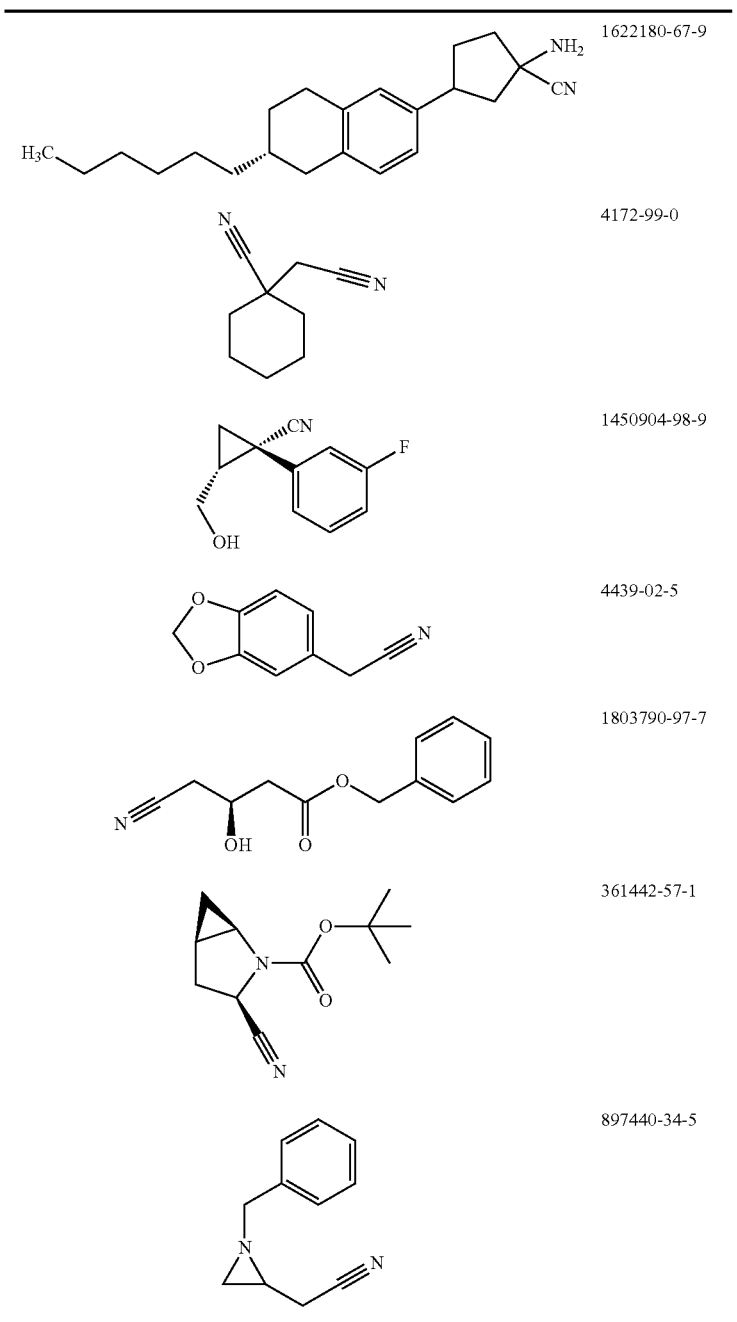

| | |
|---|---|
| | 1622180-67-9 |
| | 4172-99-0 |
| | 1450904-98-9 |
| | 4439-02-5 |
| | 1803790-97-7 |
| | 361442-57-1 |
| | 897440-34-5 |

In the microbiological process object of the present invention the enzyme can be used in purified form or as component of the bacterial biomass. Optionally the enzyme can be also used in immobilized form according to conventional techniques, for example onto a solid-type substrate.

Preferably the enzyme is used in the form of a biomass as a paste having then a dry residue at 105° C. within a range from 20 to 45%, preferably from 25 to 40%.

The enzyme can be also used in the form of a dried/lyophilized biomass having a dry residue at 105° C. from 90 to 100%, preferably from 95 to 99%.

The amount of enzyme can vary depending on the biocatalyst activity. For the biocatalyst as a paste at 25% the amount can range from 2 g to 8 g, preferably from 3 to 6 g, to obtain 1 Kg ADM at 100%. For the lyophilized biomass instead, about from 0.5 to 2 g, preferably from 0.75 g to 1.5 g, are used to obtain the same quantity.

The process object of the present invention is carried out in aqueous solution, preferably in the presence of an organic co-solvent.

The function of the co-solvent is mainly that to enhance the dissolution of the nitrile and/or amide. Therefore, the type of co-solvent and its amount will depend on the characteristics of the nitrile to be hydrolyzed and of the amide to be obtained and they could be changed based on the knowledge of the skilled in the art.

Indicatively, the co-solvent will be selected among methanol, ethanol, tetrahydrofuran, methyl-tetrahydrofuran, 1,4-dioxane, toluene, t.BuOMe.

Methanol and toluene are particularly preferred.

The amount of co-solvent is generally between 2% and 20% v/v, preferably between 5% and 15%, still more preferably about 10%.

Also the selection of the other process conditions, such as temperature and pH, are within the knowledge of the skilled in the art.

In general, the preferred pH range within which the process object of the present invention is carried out is from 6.0 to 9.0. More preferably the pH range is from 6.5 to 7.5.

The desired pH value is obtained by using a suitable buffer in the reaction mixture.

The use of phosphate buffer is particularly preferred.

Even preferably and advantageously working at room temperature, also the reaction temperature can vary depending on the substrate to hydrolyze to promote the conversion rate. In general the temperature could range from 10 to 45° C., preferably from 15 to 30° C.

The very high flexibility of the process object of the present invention which allows to obtain a good conversion of a wide variety of nitriles, including nitriles with a complex structure such as plurisubstituted compounds, dinitriles, chiral compounds, will been still more apparent from the results of the following examples which, however, have no limitative purpose of the scope of the invention.

EXAMPLES

The reactions were carried out in phosphate buffer (10 mM, pH=7.4) using 10% of co-solvent to increase the nitrile solubility.

General procedure: the substrate (final concentration 50 mM) was added in 1 mL of MeOH to a suspension of the enzyme (NHase 4 mg) in buffer (9 mL). In order to ensure the dissolution, sonication or heating were applied, if needed. The reactions were followed in time (1 mL samples) by different analytical methods. Every sample was quenched with MeOH, filtered and analyzed.

Example 1

2-Chloroacetamide

NHase was grinded in a mortar and added to a potassium phosphate buffer (10 mM, pH=7.4) (9 mL) in a 50 mL Erlenmeyer. The suspension was mixed by vortex and 2-chloroacetonitrile (38 mg, 0.5 mmol) was added to the suspension dissolved in MeOH (1 mL). The reaction was stirred by orbital shaking at 25° C. and 250 rpm. The reaction was followed by $^1$H-NMR. Samples (1 mL) were analyzed after 1.5, 2.5, 4 and 7 hours.

Samples were mixed with MeOH (2 mL), filtered and evaporated under vacuum. Total conversion towards 2-chloroacetamide was observed after 1.5 hours.

$^1$H-NMR (CD$_3$OD, 300.13 MHz): 4.05-4.83 (s, 2H), comparable to a commercially available sample of 2-chloroacetamide.

Example 2

2,2-Diethoxyacetamide

NHase was grinded in a mortar and added to a potassium phosphate buffer (10 mM, pH=7.4) (9 mL) in a 50 mL Erlenmeyer. The suspension was mixed by vortex and 2,2-diethoxyacetonitrile (65 mg, 0.5 mmol) was added to the suspension dissolved in MeOH (1 mL). The reaction was stirred by orbital shaking at 25° C. and 250 rpm. The reaction was followed by $^1$H-NMR. Samples (1 mL) were analyzed after 1.5, 2.5, 4 and 7 hours. Samples were mixed with MeOH (2 mL), filtered and evaporated under vacuum. Total conversion towards 2,2-diethoxyacetamide was observed after 1.5 hours.

$^1$H-NMR (CD$_3$OD, 300.13 MHz): 1.44 (t, 6 H, $^3J_{HH}$=6.0 Hz), 3.61-3.70 (m, 4 H), 4.81 (s, 1 H), comparable to a commercially available sample of 2,2-diethoxyacetamide.

Example 3 tert-Butyl 4-carbamoylpiperidin-1-carboxylate

NHase was grinded in a mortar and added to a potassium phosphate buffer (10 mM, pH=7.4) (9 mL) in a 50 mL Erlenmeyer. The suspension was mixed by vortex and tert-butyl 4-cyanopiperidin-1-carboxylate (105 mg, 0.5 mmol) was added to the suspension dissolved in MeOH (1 mL). The reaction was stirred by orbital shaking at 25° C. and 250 rpm. The reaction was followed by HPLC-MS. Samples (1 mL) were analyzed after 1.5, 2.5, 4 and 7 hours. Samples were mixed with MeOH (2 mL), filtered and directly injected to the HPLC. 40% conversion towards tert-butyl 4-carbamoylpiperidin-1-carboxylate was observed after 7 hours.

MS (ES$^+$): m/z: 173.0 [M-55]. MS (ES$^-$): m/z: 227.0 [M-1].

The HPLC chromatogram was comparable to a synthetized sample of tert-butyl 4-carbamoylpiperidin-1-carboxylate. RRT$_3$=1, RRT$_{3a}$=0.87.

Example 4

2-(Phenylsulfonyl)acetamide

NHase was grinded in a mortar and added to a potassium phosphate buffer (10 mM, pH=7.4) (9 mL) in a 50 mL Erlenmeyer. The suspension was mixed by vortex and 2-(phenylsulfonyl)acetonitrile (91 mg, 0.5 mmol) was added to the suspension dissolved in MeOH (1 mL). The reaction was stirred by orbital shaking at 25° C. and 250 rpm. The reaction was followed by HPLC-MS. Samples (1 mL) were analyzed after 1.5, 2.5, 4 and 7 hours. Samples were mixed with MeOH (2 mL), filtered and directly injected to the HPLC.

MS (ES$^+$): m/z: 200.1 [M+1], 217.1 [M+18]. RRT$_{4a}$=0.36.

Example 5

Methyl 3-amino-3-oxopropanoate

NHase was grinded in a mortar and added to a potassium phosphate buffer (10 mM, pH=7.4) (9 mL) in a 50 mL Erlenmeyer. The suspension was mixed by vortex and methyl 2-cyanoacetate (91 mg, 0.5 mmol) was added to the suspension dissolved in MeOH (1 mL). The reaction was stirred by orbital shaking at 25° C. and 250 rpm. The reaction was followed by HPLC-MS and $^1$H-NMR. Samples (1 mL) were analyzed after 1.5, 2.5, 4 and 7 hours. Samples were mixed with MeOH (2 mL), filtered and directly injected to the HPLC. The rest of the sample that was not injected was evaporated under vacuum and analyzed by $^1$H-NMR. Total conversion was observed after 1.5 hours.

$^1$H-NMR (CD3OD, 300.13 MHz): 3.77 (s, 2 H), 3.98 (s, 3 H). MS (ES$^+$): m/z: 118.1 [M+1].

Example 6

3-(Phenylamino)propanamide

NHase was grinded in a mortar and added to a potassium phosphate buffer (10 mM, pH=7.4) (9 mL) in a 50 mL Erlenmeyer. The suspension was mixed by vortex and 3-(phenylamino)propanenitrile (73 mg, 0.5 mmol) was added to the suspension dissolved in MeOH (1 mL). The reaction was stirred by orbital shaking at 25° C. and 250 rpm. The reaction was followed by HPLC-MS. Samples (1 mL) were analyzed after 1.5, 2.5, 4 and 7 hours. Samples were mixed with MeOH (2 mL), filtered and directly injected to the HPLC. Total conversion was observed after 2.5 hours. MS (ES$^+$): m/z: 165.1 [M+1]. RRT$_8$=1, RRT$_{8a}$=0.51.

Example 7

3,3-Dimethoxypropanamide

NHase was grinded in a mortar and added to a potassium phosphate buffer (10 mM, pH=7.4) (9 mL) in a 50 mL Erlenmeyer. The suspension was mixed by vortex and 3,3-dimethoxypropanenitrile (58 mg, 0.5 mmol) was added to the suspension dissolved in MeOH (1 mL). The reaction was stirred by orbital shaking at 25° C. and 250 rpm. The reaction was followed by GC-MS. Samples (1 mL) were analyzed after 1.5, 2.5, 4 and 7 hours. Samples were mixed with MeOH (2 mL) and filtered. Water (2 mL) was added to the sample and the samples were extracted with EtOAc (4 mL). The organic phase was dried over Na$_2$SO$_4$, filtered and directly injected to the GC-MS. Almost total conversion was observed after 7 hours.

MS (ES+): m/z: 156.1 [M+23]. RRT$_9$=1, RRT$_{9a}$=1.22.

Example 8

2-(2-Aminophenyl)acetamide NHase was grinded in a mortar and added to a potassium phosphate buffer (10 mM, pH=7.4) (9 mL) in a 50 mL Erlenmeyer. The suspension was mixed by vortex and 2-(2-aminophenyl)acetonitrile (66 mg, 0.5 mmol) was added to the suspension dissolved in MeOH (1 mL). The reaction was stirred by orbital shaking at 25° C. and 250 rpm. The reaction was followed by HPLC-MS. Samples (1 mL) were analyzed after 1.5, 2.5, 4 and 7 hours. Samples were mixed with MeOH (2 mL), filtered and directly injected to the HPLC. Total conversion was observed after 2.5 hours.

MS (ES$^+$): m/z: 151.1 [M+1]. RRT$_{10}$=1, RRT$_{10a}$=0.48.

Example 9

2-Amino-2-oxoacetohydrazide

NHase was grinded in a mortar and added to a potassium phosphate buffer (10 mM, pH=7.4) (9 mL) in a 50 mL Erlenmeyer. The suspension was mixed by vortex and 2-cyanoacetohydrazide (50 mg, 0.5 mmol) was added to the suspension dissolved in MeOH (1 mL). The reaction was stirred by orbital shaking at 25° C. and 250 rpm. The reaction was followed by $^1$H-NMR. Samples (1 mL) were analyzed after 1.5, 2.5, 4 and 7 hours. Samples were mixed with MeOH (2 mL), filtered, evaporated under vacuum and analyzed by $^1$H-NMR. Total conversion was observed after 1.5 hours.

$^1$H-NMR (CD$_3$OD, 300.13 MHz): 3.48-3.58 (m, 2 H).

Example 10

2-(2-Cyanophenyl)acetamide

NHase was grinded in a mortar and added to a potassium phosphate buffer (10 mM, pH=7.4) (9 mL) in a 50 mL Erlenmeyer. The suspension was mixed by vortex and 2-(cyanomethyl)benzonitrile (71 mg, 0.5 mmol) was added to the suspension dissolved in MeOH (1 mL). The reaction was stirred by orbital shaking at 25° C. and 250 rpm. The reaction was followed by HPLC-MS and $^1$H-NMR. Samples (1 mL) were analyzed after 1.5, 2.5, 4 and 7 hours. Samples were mixed with MeOH (2 mL), filtered and directly injected to the HPLC. The rest of the sample that was not injected was evaporated under vacuum and analyzed by $^1$H-NMR. Total conversion was observed after 1.5 hours.

$^1$H-NMR (CD$_3$OD, 300.13 MHz): 3.81 (s, 2 H), 7.49 (t, 2 H, $^3$J$_{HH}$=7.6 Hz), 7.70 (d, 2 H, $^3$J$_{HH}$=7.6 Hz).

MS (ES$^+$): m/z: 161.1 [M+1]

Example 11

2-(Isopropylsulfonyl)acetamide

NHase was grinded in a mortar and added to a potassium phosphate buffer (10 mM, pH=7.4) (9 mL) in a 50 mL Erlenmeyer. The suspension was mixed by vortex and 2-(isopropylsulfonyl)acetonitrile (74 mg, 0.5 mmol) was added to the suspension dissolved in MeOH (1 mL). The reaction was stirred by orbital shaking at 25° C. and 250 rpm. The reaction was followed by HPLC-MS and $^1$H-NMR. Samples (1 mL) were analyzed after 1.5, 2.5, 4 and 7 hours. Samples were mixed with MeOH (2 mL), filtered and directly injected to the HPLC. The rest of the sample that was not injected was evaporated under vacuum and analyzed by $^1$H-NMR. Total conversion was observed after 1.5 hours.

$^1$H-NMR (CD$_3$OD, 300.13 MHz): 1.35 (s, 3 H), 1.38 (s, 1 H), 3.52-3.61 (m, 1 H), 4.60 (s, 2 H, overlapped with the water of CD$_3$OD).

MS (ES$^+$): m/z: 166.1 [M+1]. RRT$_{14}$=1, RRT$_{14a}$=0.54.

Example 12

Ethyl (R)-5-amino-3-hydroxy-5-oxopentanoate

NHase was grinded in a mortar and added to a potassium phosphate buffer (10 mM, pH=7.4) (9 mL) in a 50 mL Erlenmeyer. The suspension was mixed by vortex and ethyl (R)-4-cyano-3-hydroxybutanoate (79 mg, 0.5 mmol) was added to the suspension dissolved in MeOH (1 mL). The reaction was stirred by orbital shaking at 25° C. and 250 rpm. The reaction was followed by $^1$H-NMR. Samples (1 mL) were analyzed after 1.5, 2.5, 4 and 7 hours. Samples were mixed with MeOH (2 mL), filtered, evaporated under vacuum and analyzed by $^1$H-NMR. 34% Conversion was observed after 7 hours.

$^1$H-NMR (CD$_3$OD, 300.13 MHz): 1.35 (t, 3 H, $^3$J$_{HH}$=2.3 Hz), 2.41-2.77 (4 H, m, overlapped with the signals of the starting compound), 3.70 (s, 2 H), 4.40-4.43 (m, 1 H).

MS (ES$^+$): m/z: 176.1 [M+1].

Example 13

N$^1$-Phenylmalonamide

NHase was grinded in a mortar and added to a potassium phosphate buffer (10 mM, pH=7.4) (8 mL) in a 50 mL Erlenmeyer. The suspension was mixed by vortex and 2-cyano-N-phenylacetamide (80 mg, 0.5 mmol) was added to the suspension dissolved in MeOH (1 mL). The reaction was stirred by orbital shaking at 25° C. and 250 rpm. The reaction was followed by HPLC-MS. Samples (1 mL) were analyzed after 1.5, 2.5, 4 and 7 hours. Samples were mixed with MeOH (2 mL), filtered and directly injected to the HPLC. Low conversion (13%) was observed after 4 hours.

MS (ES$^+$): m/z: 176.9 [M–1]. RRT$_{17}$=1, RRT$_{17a}$=0.61.

Example 14

Methyl 1-carbamoylcyclopentan-1-carboxylate

NHase was grinded in a mortar and added to a potassium phosphate buffer (10 mM, pH=7.4) (9 mL) in a 50 mL Erlenmeyer. The suspension was mixed by vortex and methyl 1-cyanocyclopentan-1-carboxylate (77 mg, 0.5 mmol) was added to the suspension dissolved in MeOH (1 mL). The reaction was stirred by orbital shaking at 25° C. and 250 rpm. The reaction was followed by GC-MS. Samples (1 mL) were analyzed after 1.5, 2.5, 4 and 7 hours. Samples were mixed with MeOH (2 mL) and filtered. Water (2 mL) was added to the sample and the samples were extracted with EtOAc (4 mL). The organic phase was dried over Na$_2$SO$_4$, filtered and directly injected to the GC-MS. About 72% conversion was observed after 7 hours.

MS (ES$^+$): m/z: 171.9 [M+1]. RRT$_{19}$=1, RRT$_{19a}$=1.11.

Example 15

6-Bromo-2,2-dimethylhexanamide

NHase was grinded in a mortar and added to a potassium phosphate buffer (10 mM, pH=7.4) (9 mL) in a 50 mL Erlenmeyer. The suspension was mixed by vortex and 6-bromo-2,2-dimethylhexanenitrile (102 mg, 0.5 mmol) was added to the suspension dissolved in MeOH (1 mL). The reaction was stirred by orbital shaking at 25° C. and 250 rpm. The reaction was followed by GC-MS. Samples (1 mL) were analyzed after 1.5, 2.5, 4 and 7 hours. Samples were mixed with MeOH (2 mL) and filtered. Water (2 mL) was added to the sample and the samples were extracted with EtOAc (4 mL). The organic phase was dried over Na$_2$SO$_4$, filtered and directly injected to the GC-MS. About 64% conversion was observed after 7 hours.

MS (ES+): m/z: 223.9 [M+1]. RRT$_{20}$=1, RRT$_{20a}$=1.12.

Example 16

(E)-5-Cyanopent-3-enamide

NHase was grinded in a mortar and added to a potassium phosphate buffer (10 mM, pH=7.4) (9 mL) in a 50 mL Erlenmeyer. The suspension was mixed by vortex and (E)-hex-3-enedinitrile (53 mg, 0.5 mmol) was added to the suspension dissolved in MeOH (1 mL). The reaction was stirred by orbital shaking at 25° C. and 250 rpm. The reaction was followed by $^1$H-NMR. Samples (1 mL) were analyzed after 1.5, 2.5, 4 and 7 hours. Samples were mixed with MeOH (2 mL), filtered, evaporated under vacuum and analyzed by $^1$H-NMR. 97% Conversion was observed after 1.5 hours. From the $^1$H-NMR spectrum the presence of the corresponding diamide in a percentage of about 7% can be hypothesized.

$^1$H-NMR (CD$_3$OD, 300.13 MHz): 3.00-3.19 (m, 2 H), 3.21-3.30 (m, 2 H), 5.55-5.50 (m, 1 H), 5.90-6.00 (m, 1 H). MS (ES$^+$): m/z: 142.1 [M+18].

Example 17

2-((Cyanomethyl)amino)acetamide

NHase was grinded in a mortar and added to a potassium phosphate buffer (10 mM, pH=7.4) (9 mL) in a 50 mL Erlenmeyer. The suspension was mixed by vortex and 2,2'-azanediyldiacetonitrile (48 mg, 0.5 mmol) was added to the suspension dissolved in MeOH (1 mL). The reaction was stirred by orbital shaking at 25° C. and 250 rpm. The reaction was followed by $^1$H-NMR. Samples (1 mL) were analyzed after 1.5, 2.5, 4 and 7 hours. Samples were mixed with MeOH (2 mL), filtered, evaporated under vacuum and analyzed by $^1$H-NMR. Total conversion was observed after 1.5 hours. From the $^1$H-NMR spectrum the presence of the corresponding diamide (about 30%) cab be hypothesized.

$^1$H-NMR (CD3OD, 300.13 MHz): 3.336 (s, 2 H), 3.68 (s, 2 H).

MS (ES$^+$): m/z: 113.9 [M+1].

Example 19

N$^1$-Benzylmalonamide

NHase was grinded in a mortar and added to a potassium phosphate buffer (10 mM, pH=7.4) (9 mL) in a 50 mL Erlenmeyer. The suspension was mixed by vortex and N-benzyl-2-cyanoacetamide (80 mg, 0.5 mmol) was added to the suspension dissolved in MeOH (1 mL). The reaction was stirred by orbital shaking at 25° C. and 250 rpm. The reaction was followed by HPLC-MS. Samples (1 mL) were analyzed after 1.5, 2.5, 4 and 7 hours. Samples were mixed with MeOH (2 mL), filtered and directly injected to the HPLC. 80% Conversion was observed after 4 hours.

MS (ES$^+$): m/z: 193.1 [M+1]. RRT$_{25}$=1, RRT$_{25a}$=0.65.

Example 20

2-Phenylacetamide

NHase (4 mg) was added to a solution of 2-phenylacetonitrile (59 mg, 0.5 mmol) in potassium phosphate buffer (10 mM, 1% MeOH, pH=7.4) (10 mL) in a 50 mL Erlenmeyer. The reaction was stirred by orbital shaking at 25° C. Samples (200 μL) were measured by HPLC-MS and $^1$H-NMR. The reaction was stopped after 4 hours. Reactions were extracted with DCM (15 mL×2). The organic layers were combined, dried over Na$_2$SO$_4$, filtered and evaporated under vacuum. 2-Phenylacetamide was isolated in 37% yield as a white solid.

$^1$H-NMR (CDCl$_3$, 300.13 MHz): 3.70 (s, 2 H), 5.16 (bs, 1 H), 5.73 (bs, 1 H), 7.27-7.43 (m, 5 H).

Example 21

3-Phenylpropanamide

NHase (4 mg) was added to a solution of 3-phenylpropanenitrile (66 mg, 0.5 mmol) in potassium phosphate buffer (10 mM, 1% MeOH, pH=7.4) (10 mL) in a 50 mL Erlenmeyer. The reaction was stirred by orbital shaking at 25° C. Samples (200 μL) were measured by HPLC-MS and $^1$H-NMR. The reaction was stopped after 4 hours.

Reactions were extracted with DCM (15 mL×2). The organic layers were combined, dried over Na$_2$SO$_4$, filtered and evaporated under vacuum. 3-Phenylpropanamide was isolated in 99% yield as a white solid. $^1$H-NMR (CDCl$_3$, 300.13 MHz): 2.55 (t, 2 H, $^3J_{HH}$=8.2 Hz), 3.00 (t, 2 H, $^3J_{HH}$=8.2 Hz), 5.16-5.47 (bs, 1 H), 5.73 (bs, 1 H), 7.17-7.36 (m, 5 H).

Example 22

Ethyl 3-amino-3-oxo-2-phenylpropanoate

NHase (4 mg) was added to a solution of (±) ethyl 2-cyano-2-phenylacetate (59 mg, 0.5 mmol) in potassium phosphate buffer (10 mM, 1% toluene, pH=7.4) (10 mL) in a 50 mL Erlenmeyer. The reaction was stirred by orbital shaking at 25° C. Samples (500 μL) were extracted with DCM and measured by UPC-MS. The reaction was analyzed at different times. The conversion observed in these conditions after one hour was 30% and ethyl 3-amino-3-oxo-2-phenylpropanoate was obtained with 97% ee.

The comparison with the ¹H-NMR spectrum of the amide obtained by synthetic route confirmed the structure.

Example 23

2-Phenylpropanamide

NHase (4 mg) was added to a solution of (±) 2-phenyl-propanenitrile (66 mg, 0.5 mmol) in potassium phosphate buffer (10 mM, 1% toluene, pH=7.4) (10 mL) in a 50 mL Erlenmeyer. The reaction was stirred by orbital shaking at 25° C. Samples (500 μL) were extracted with DCM and measured by GC-MS. The reaction was analyzed at different times. The conversion observed in these conditions after one hour was 83% and (S)-2-phenylpropanamide was obtained with 82% ee.

The comparison with the ¹H-NMR spectrum of the amide obtained by synthetic route confirmed the structure.

Example 24

5-Cyanopentanamide

NHase (16 mg) was grinded in a mortar and added to demineralized water (40 mL) in a 100 mL Erlenmeyer. The suspension was mixed by vortex and adiponitrile (224 μL, 0.5 mmol) was added to this suspension dissolved in toluene (400 4). The reaction was stirred by orbital stirring at 25° C. and 250 rpm. The reaction was followed by GC-MS. Samples (1 mL) were analyzed in time. Samples were mixed with MeOH (2 mL), filtered, evaporated under vacuum and dissolved in MeOH. 5-Cyanopentanamide (92 mg) was isolated in 37% yield.

$RRT_{amide}=1.12$, $RRT_{nitrile}=1$.

¹H-NMR (CD₃OD, 300.13 MHz): 1.59-1.84 (m, 4H), 2.26 (t, 2H, ³$J_{HH}$=7.0 Hz), 2.49 (t, 2H, ³$J_{HH}$=7.0 Hz).

MS (EI): m/z: 126.1 [M]

The invention claimed is:

1. A process for the preparation of amides of formula

R(R')(R'')C—CONH2    (I)

comprising the reaction of a nitrile of formula

R(R')(R'')C—CN    (II)

with the nitrile hydratase enzyme produced by the bacterial strain *Rhodococcus* biphenylivorans named "Palladio 22" deposited in the Collection of Microorganisms BCCM-LMG with deposit number LMG P-29520, wherein at least one of R, R' and R" is not hydrogen;

R, R' and R", are the same or different from each other, and are independently selected from the group consisting of hydrogen, $C_1$-$C_6$ alkyl, $C_1$-$C_6$ alkoxy, $C_1$-$C_6$ alkoxycarbonyl, $C_2$-$C_6$ alkenyl, $C_3$-$C_6$ cycloalkyl optionally containing a =O group, R' "CO—, heterocycle with 3 to 6 atoms, wherein one of these atoms is N or O, arylsulfonyl, $C_1$-$C_6$ alkylsulfonyl, aryl, arylaminocarbonyl and $C_1$-$C_6$ alkylaminocarbonyl;

R''' is $C_1$-$C_6$ alkyl, aryl, amino, or hydrazino; and each of R, R', R", when not hydrogen, and R''' are optionally substituted by one or more substituents selected from the group consisting of halogen, nitrile, amino, $C_1$-$C_6$ alkylamino, hydroxy, $C_1$-$C_6$ alkoxy, and aryl groups;

provided that the compound of formula I is not acrylamide.

2. The process according to claim 1, wherein at least one of R, R', R" and R''' is or contains a functional group sensitive to hydrolysis or solvolysis under acid, basic or neutral catalysis or environment is selected from the group consisting of an additional nitrile group, an ester group, an amide group, a haloalkyl group, and an ammonium salt.

3. The process according to claim 1, wherein said process is carried out in aqueous solution, and optionally in the presence of an organic co-solvent.

4. The process according to claim 3, wherein the co-solvent is selected from the group consisting of methanol, ethanol, tetrahydrofuran, methyl-tetrahydrofuran, 1,4-dioxane, toluene, and methyl tert-butyl ether.

5. The process according to claim 3 wherein the amount of co-solvent is between 2% and 20% v/v.

6. The process according to claim 1, wherein the reaction is carried out at a pH from 6.0 to 9.0.

7. The process according to claim 1, wherein the reaction is carried out at a temperature from 10 to 45° C.

8. The process according to claim 4, wherein the co-solvent is methanol or toluene.

9. The process according to claim 5, wherein the amount of co-solvent is between 5% and 15%.

10. The process according to claim 9, wherein the amount of co-solvent is about 10%.

11. The process according to claim 6, wherein the reaction is carried out at a pH from 6.5 to 7.5.

12. The process according to claim 7, wherein the reaction is carried out at a temperature from 15 to 30° C.

\* \* \* \* \*